United States Patent
Rosenblatt

(10) Patent No.: US 8,079,963 B2
(45) Date of Patent: Dec. 20, 2011

(54) ELECTRICAL DETECTION OF ANATOMIC WALL PENETRATION AND DELINEATION OF ATOMIC STRUCTURES DURING SURGERY

(75) Inventor: Peter L. Rosenblatt, Newton, MA (US)

(73) Assignee: Rosenblatt Associates, LLC, West Newton, MA (US)

( * ) Notice: Subject to any disclaimer, the term of this patent is extended or adjusted under 35 U.S.C. 154(b) by 0 days.

(21) Appl. No.: 12/747,782

(22) PCT Filed: Dec. 12, 2008

(86) PCT No.: PCT/US2008/086632
§ 371 (c)(1),
(2), (4) Date: Jun. 14, 2010

(87) PCT Pub. No.: WO2009/076616
PCT Pub. Date: Jun. 18, 2009

(65) Prior Publication Data
US 2010/0286482 A1 Nov. 11, 2010

Related U.S. Application Data

(60) Provisional application No. 61/007,300, filed on Dec. 12, 2007.

(51) Int. Cl.
- A61B 1/32 (2006.01)
- A61B 5/05 (2006.01)
- A61B 5/103 (2006.01)
- A61B 5/117 (2006.01)
- A61B 17/42 (2006.01)
- A61B 19/00 (2006.01)
- A61M 29/00 (2006.01)

(52) U.S. Cl. ........ 600/591; 600/202; 600/547; 600/587; 606/119; 606/129; 606/191; 606/192; 606/193; 606/197

(58) Field of Classification Search .......... 600/202, 600/547, 587, 591; 606/119, 129, 191–193, 606/197
See application file for complete search history.

(56) References Cited

U.S. PATENT DOCUMENTS

| | | | | |
|---|---|---|---|---|
| 3,791,385 A * | 2/1974 | Davis et al. | ...................... | 604/12 |
| 4,909,263 A * | 3/1990 | Norris | ............... | 607/39 |
| 5,209,754 A * | 5/1993 | Ahluwalia | ................. | 600/207 |
| 5,301,658 A * | 4/1994 | Zhu et al. | ...................... | 600/202 |
| 5,578,048 A | 11/1996 | Pasqualucci et al. | | |
| 5,643,285 A * | 7/1997 | Rowden et al. | .............. | 606/119 |
| 5,746,224 A * | 5/1998 | Edwards | ....................... | 128/898 |
| 6,081,749 A * | 6/2000 | Ingle et al. | ................... | 607/101 |
| 6,210,314 B1 * | 4/2001 | Ein-Gal | ............................ | 600/3 |
| 6,423,075 B1 | 7/2002 | Singh et al. | | |
| 6,546,934 B1 * | 4/2003 | Ingle et al. | ..................... | 128/898 |
| 6,558,381 B2 * | 5/2003 | Ingle et al. | .................... | 606/41 |
| 6,625,495 B1 | 9/2003 | Alon et al. | | |
| 6,629,535 B2 * | 10/2003 | Ingle et al. | ................... | 128/898 |
| 6,709,380 B2 * | 3/2004 | Green et al. | ...................... | 600/3 |
| 6,912,416 B2 | 6/2005 | Rosenblatt | | |
| 7,079,882 B1 * | 7/2006 | Schmidt | ........................ | 600/373 |
| 7,722,538 B2 * | 5/2010 | Khoury | ........................ | 600/438 |
| 2001/0018606 A1 * | 8/2001 | Ingle et al. | ................... | 607/116 |
| 2003/0178032 A1 * | 9/2003 | Ingle et al. | ................... | 128/898 |
| 2005/0085827 A1 | 4/2005 | Najera et al. | | |

* cited by examiner

OTHER PUBLICATIONS

International Search Report and Written Opinion for PCT/US2008/086632 dated Jun. 24, 2009.

*Primary Examiner* — Max Hindenburg
*Assistant Examiner* — Sean Dougherty
(74) *Attorney, Agent, or Firm* — Scott E. Kamholz; Foley Hoag LLP

(57) ABSTRACT

Devices and methods that may be employed to detect and/or prevent intraoperative full thickness penetration of anatomic walls, and to provide delineation of anatomic structures during surgery.

8 Claims, 4 Drawing Sheets

ELECTRICAL DETECTION OF ANATOMIC WALL PENETRATION AND DELINEATION OF ATOMIC STRUCTURES DURING SURGERY

CROSS-REFERENCE TO RELATED APPLICATION

This is the national stage of International Application Ser. No. PCT/US2008/086632, filed Dec. 12, 2008, which claims the benefit of U.S. Provisional Application No. 61/007,300, filed Dec. 12, 2007, which is hereby incorporated herein by reference.

BACKGROUND

Pelvic reconstructive surgery often involves placing sutures into endopelvic fascia. These procedures can be performed abdominally or laparoscopically. For the purposes of this discussion, a laparoscopic approach will be described, but it should be understood that these principles may apply to abdominal surgery as well. Procedures that are used for reconstructive pelvic surgery include uterosacral ligament suspension, paravaginal repair, Burch colposuspension, sacrocolpopexy, and sacrocervicopexy. When performing these procedures, most surgeons prefer to avoid penetration of the vaginal lumen. This is especially true when mesh is used for reconstructive surgery. Suture penetration may increase the risk of mesh erosion. Some surgeons place a hand in the vagina in an attempt to avoid vaginal penetration. Other surgeons use vaginal probes, Lucite molds or end-to-end anastomotic (EEA) sizers placed in the vagina and suturing is performed over these devices. More recently, robotic surgery has been used in gynecologic reconstructive surgery, which deprives the surgeon of the tactile sensation that can be used to avoid vaginal penetration of suture material. In addition, the bladder and rectum are adjoining structures that may be injured during suturing in the endopelvic fascia. Most surgeons use vaginal probes that are essentially cylindrical, elongated solid devices with a rounded tip. Some probes, such as the vaginal probe from Apple Medical, and the EEA sizers, have a distal end with a defined diameter that is attached to a handle by a narrow rod.

SUMMARY

The disclosed devices and methods may be employed to detect and/or prevent intraoperative full thickness penetration of anatomic walls, and to provide delineation of anatomic structures during surgery. For example, a probe that is shaped to conform to an anatomic structure is placed in that anatomic structure. The probe has a conductive surface and is electrically connected to an electrical meter. A needle or other penetrative device for surgical use is also electrically connected to the electrical meter. A source of electricity (such as a battery) is electrically connected to at least one of the probe, penetrative device, and meter. The probe, penetrative device, meter, electricity source, and electrical connections therebetween form an electrical circuit if the probe and penetrative device become electrically connected, such as by full-thickness penetration of the penetrative device through the wall of the anatomic structure so that the device contacts the probe or contacts a conductive medium inside the anatomic structure that itself contacts the probe. A surgeon operating adjacent the anatomic structure with the needle or other penetrative device thus can be alerted when the wall is penetrated and adjust the surgical technique accordingly. Anatomic structures include hollow organs, such as blood vessels, airways, esophagus, stomach, small intestine, large intestine, uterus, vagina, ureter, bladder, and urethra.

A probe, by conforming to an anatomic structure, can help delineate that structure to facilitate its identification and positioning during a surgical procedure.

DETAILED DESCRIPTION

Figure 1:
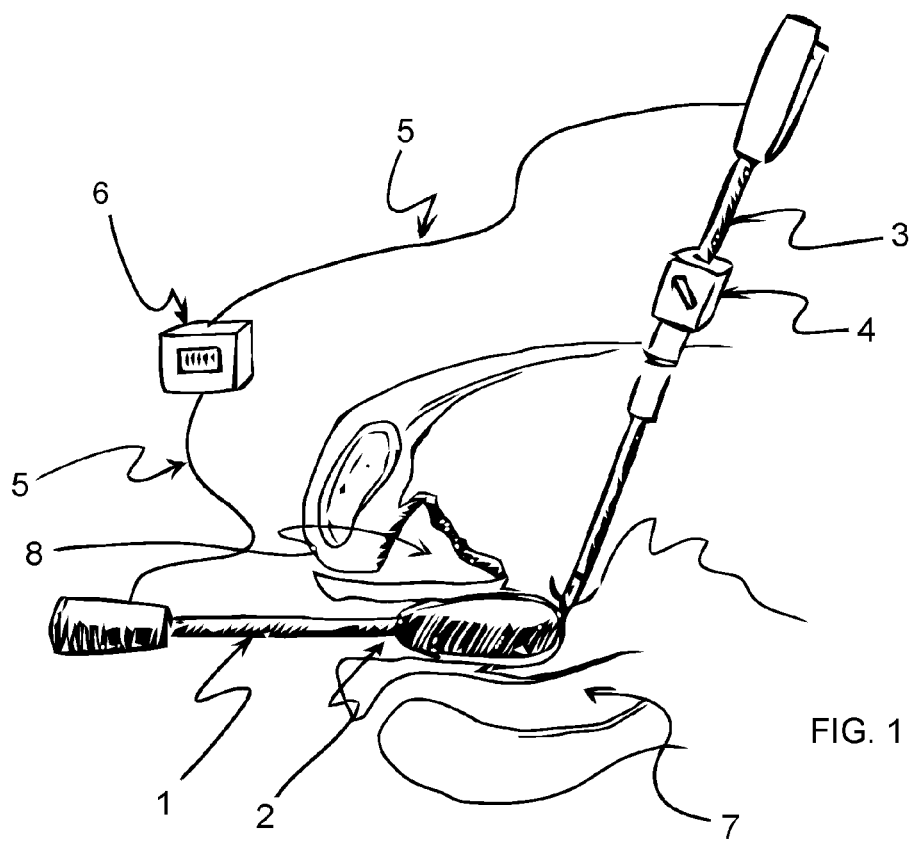
FIG. 1 shows a schematic of an electrical detection system, with an electrical device that provides a source of electricity through the circuit created by a penetrative device, such as a suture needle, and a conductive probe placed, e.g., in the vagina. The meter in the device, such as an ammeter, measures an electrical property of the system, such as the current in the circuit, and the resistance may thus be calculated to determine whether penetration of the vagina with the suture needle has occurred.

An electrical system may be used for measurement of current in a circuit to rule in or out inadvertent vaginal, bladder or rectal injury during reconstructive pelvic surgery, or injury to other organs during other types of surgery. Probes for anatomical structures may be used to delineate the structures to facilitate proper identification and suturing of tissues. Probes may be fixed to a stable structure, such as an operating table or to one another.

Although the subject matter is exemplified primarily in the context of electrical detection of vaginal penetration and delineation of pelvic structures during vaginal surgery, it is relevant in other contexts, such as surgery adjacent other hollow organs.

In one embodiment, two conductors are used, one located on a probe placed in the vagina, and the other being a needle attached to a needle driver. A source of electricity is attached to either the metallic probe in the vagina or the needle to provide electrical impulses thereto. If the needle has penetrated the vagina, a circuit will be created wherein current may be measured, and wherein resistance will be minimal. Alternatively, if the needle has not entered the vagina, the resistance provided by the vaginal wall will prevent the circuit from being created. With the application of a source of electricity to either the probe or the needle, no current will be detected. With direct current, it is known that Voltage=Current×Resistance. An electricity source may be positioned in the circuit to provide a current or a voltage across the circuit. For example, a voltage may be applied to the circuit (e.g. battery) and the current may be measured with an ammeter. In this manner, the resistance can be easily calculated, to determine whether or not the needle has penetrated the vagina. Alternatively, one may put out a fixed current and measure voltage, to determine resistance. In any event, the current measured would depend on the resistance in the tissues. The differences in resistance would be used to differentiate between a needle placed completely through the vagina and a properly placed needle in the endopelvic fascia without vaginal penetration. The same principles apply to a probe placed in the rectum, in order to prevent rectal injury. If vaginal or rectal penetration has occurred, the needle may be withdrawn and replaced. This concept may also be used to prevent injury to the bladder, as described in U.S. Pat. No. 6,912,416. Alternatively, the rectal probe could be lighted (with either an external light source with a cord that would be attached to the bowel probe, or with an internal light source that is battery operated). The electricity source could be positioned, for example, inside a probe or otherwise integrated with a probe, or integrated with another component in the circuit, or provided separately.

The electrical device may put out a fixed voltage, an ammeter measures current through the circuit, and disposable wires connect to the needle driver and vaginal probe.

An additional use for this technology involves intraoperative detection of bladder injuries during abdominal, laparoscopic or vaginal surgery. A standard needle driver (as in abdominal or vaginal surgery) or laparoscopic needle driver may be connected by a wire to the ammeter, which is also connected to metallic conductive catheter guide placed through the Foley catheter. If a small amount of conductive fluid is maintained within the bladder, then a signal will indicate whether the needle has been inadvertently placed through the bladder. In this manner, injury to the bladder may be avoided, as placement of the needle into the bladder will signal to the operator to remove the needle, before the suture is brought completely through the tissue.

The device may be part of a vaginal and rectal delineation device in which probes are placed in both the vagina and rectum, as well as in the uterus, if the patient has not had a hysterectomy. During surgery in the pelvis, it is often very useful to be able to delineate the anatomic structures such as the uterus, vagina and rectum. Examples of surgeries in which delineation of these structures is important include laparoscopic sacrocolpopexy, sacrocervicopexy, paravaginal repair, uterosacral ligament suspension, excision of endometriosis and hysterectomy.

Delineation of the vagina (post-hysterectomy) may be accomplished with a solid probe which may have an oval, biconvex, truncated biconvex, or other cross-sectional shape that conforms to the anatomy. In the case of a vaginal probe, it may be wider in the lateral dimension than the anterior-posterior dimension. The device may be tapered at the distal end to conform to the patient's anatomy. There may be several configurations that may be used to conform to the patient's anatomy. The device may have a handle located at the proximal end that may have the ability to flex and therefore antevert or retrovert the vaginal access. The probe may also have the ability to light up, in order to differentiate between the vagina and surrounding structures such as the bladder and rectum.

Delineation of the rectum may be accomplished with a solid probe which may be oval shaped and may be lighted in order to identify the location of the rectum. The rectal probe may also have the ability to conduct an electrical current in order to identify needle perforation into the rectum, as described previously. The probe may have a handle that also allows deviation of the rectum either anterior, posteriorly or laterally.

The vaginal and rectal probe handles may be capable of attaching to each other, so that they may be positioned and held in a particular configuration. For example, it may be desirable to deviate the vagina anteriorly while deflecting the rectum posteriorly. This may be useful, for example, during dissection in the rectovaginal space. These handles may also be attached to a fixed structure, such as the operating room table, so that the surgical assistant does not have to hold them for the entire case.

In patients who have a uterus, it may be useful to deviate the uterus anteriorly (antevert) or posteriorly (retrovert). For example, during dissection into the rectovaginal space, it may be useful to antevert the uterus while still having the posterior vagina and posterior fornix delineated with a probe, as well as having the rectum delineated with a posteriorly angled probe. In one embodiment, the uterine manipulator may have a narrow probe that is placed into the cervix and may be held in place by one of several methods, such as an inflatable balloon on the tip (placed inside the uterus). Alternatively, the probe could be held inside the cervix by attaching a grasping instrument (such as a tenaculum) to the external portion of the cervix and attaching this instrument to the probe. The vaginal delineator could be located on the device, or could be attached to the uterine probe, before or after placement of the uterine probe into the cervix.

For clarity and convenience, a number of exemplary embodiments will be described relating to a particular anatomic site, the female pelvis. However, it will be readily apparent to one of ordinary skill in the art that the disclosed systems and methods may be employed in a wide variety of anatomical settings to treat a broad range of abnormalities.

FIG. 1 illustrates the general design of the instrument. It includes a probe (1) placed in some hollow organ, such as the vagina (2), and connected to an instrument, such as a laparoscopic needle driver (3), which has been placed through a trocar (4). The needle driver and probe are connected to conductive wires (5) and attached to a ammeter (6) so that a determination by electrical conductance can be made that will inform the surgeon with an auditory and/or visual signal whether or not the needle has penetrated the vagina and made contact with the probe. In this figure, the rectum (7) and the bladder (8) are located adjacent to the vagina.

Figure 2:
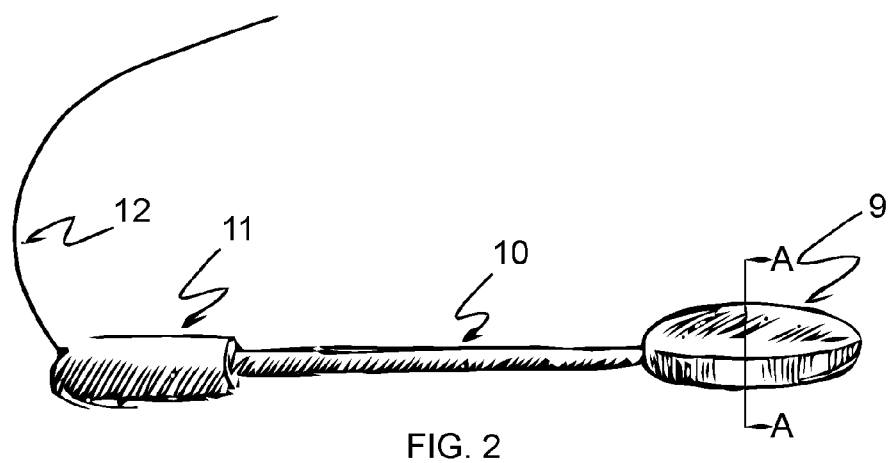
FIG. 2 illustrates one configuration of the vaginal probe, which is an oblong device that has a conducting surface anteriorly and posteriorly.
Figure 2A:
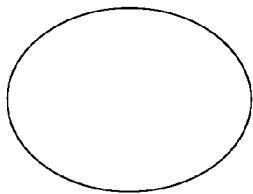
FIGS. 2A-C show exemplary alternative cross-sections taken at line A-A in FIG. 2.
Figure 2B:
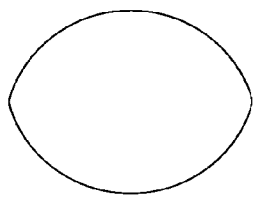
Figure 2C:
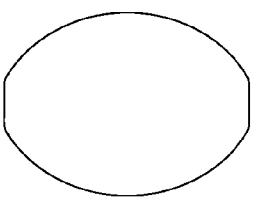

FIG. 2 illustrates the basic design of the vaginal probe, with a vaginal delineator (9) that has a conductive surface, a shaft (10), and a handle (11), to which one or more wires (12) may be attached for determination of electrical conductance. FIGS. 2A-C show exemplary alternative cross-sections taken at line A-A in FIG. 2. FIG. 2A shows an oval cross-section, FIG. 2B a biconvex cross-section, and FIG. 2C a truncated biconvex cross-section.

Figure 3:
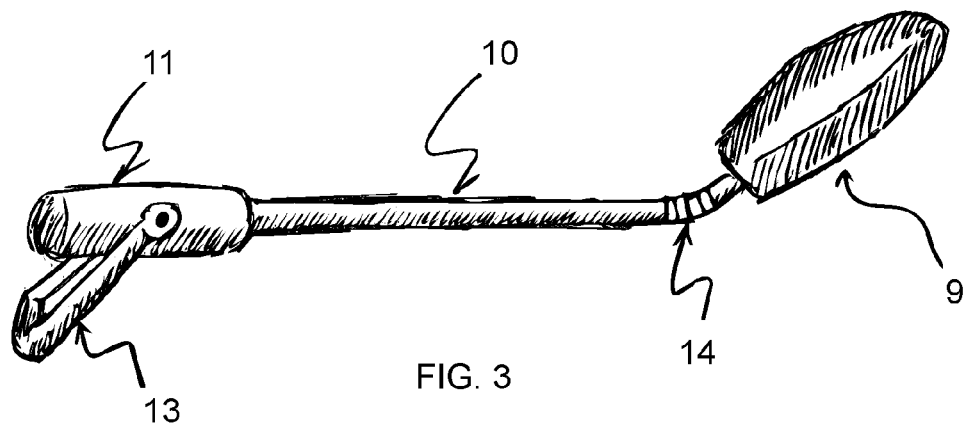
FIG. 3 illustrates the ability to tilt the vaginal probe anteriorly or posteriorly with a mechanism located on the handle of the instrument.

FIG. 3 illustrates another configuration of the vaginal probe, with the vaginal delineator (9) with a conductive surface, the shaft (10), and the handle (11) with a deflector (13), which articulates the instrument at a distal joint (14).

Figure 4:
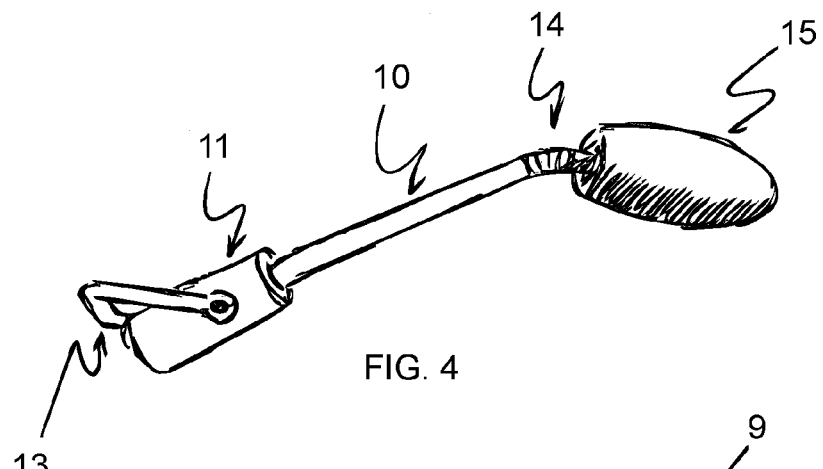
FIG. 4 illustrates one configuration of the rectal probe, which may be deflected anteriorly or posteriorly. The rectal probe may have the same electrical detection configuration and/or may be lighted (with an external or internal source).

FIG. 4 illustrates a configuration of the rectal probe, with a rectal delineator (15) with either a conductive surface or illuminated surface, the shaft (10), and the handle (11) with a deflector (13) which articulates the instrument at a distal joint (14).

Figure 5:
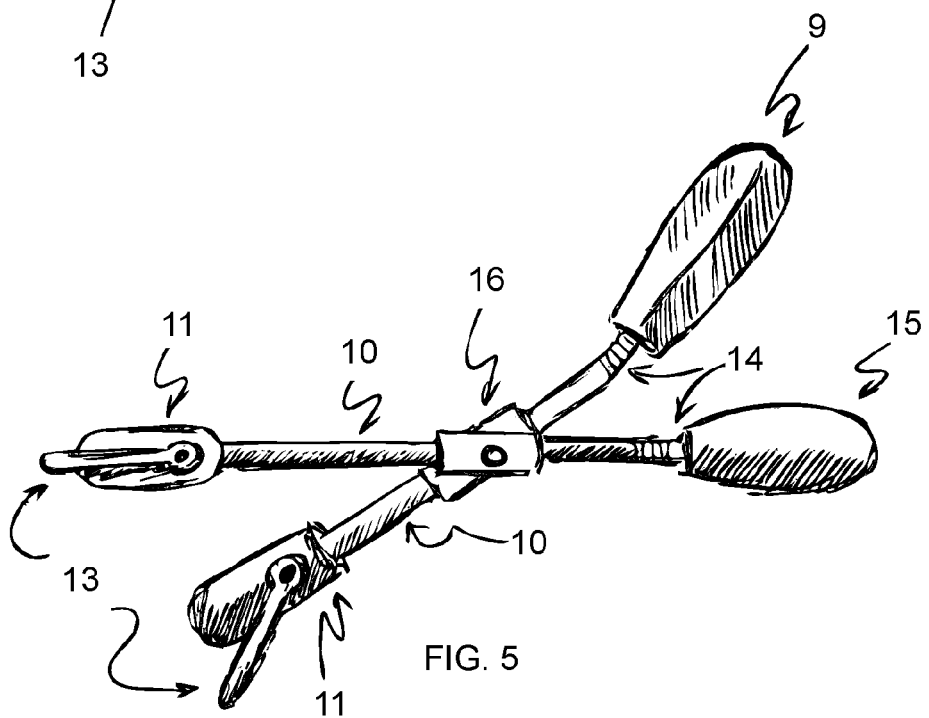
FIG. 5 illustrates another embodiment of the device where the vaginal probe and the rectal probe are attached to one another. The mechanism by which the two probes are attached may be a clip or grove in one probe, through which the other probe is placed. The angle between the two devices may be changed and locked into place.

FIG. 5 demonstrates another configuration of the device, in which the vaginal probe and the rectal probes are attached with a connector device (16), such as two short tubes that accommodate shafts (10) and are attached to one another by a pivot element. This connector may be fixed in position or may be articulated by the surgical assistant. When the connector is in the fixed position, the vaginal delineator (9) and the rectal delineator (15) may be deflected anteriorly or posteriorly at the distal joint (14) with the deflectors (13) on the handles (11).

Figure 6:
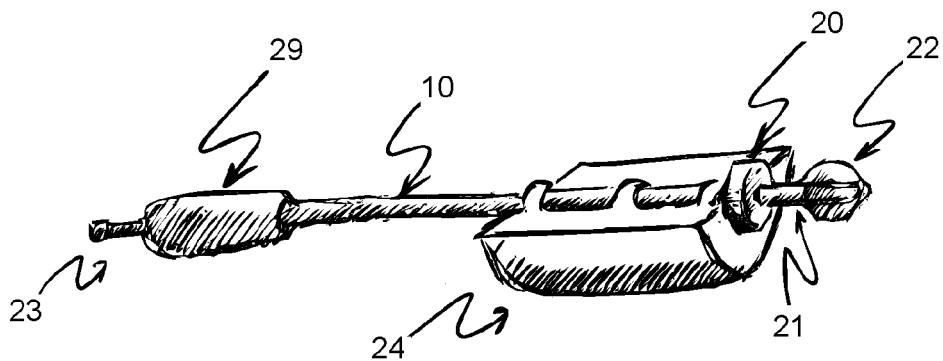
FIGS. 6 and 6A demonstrate configurations of a combined uterine/vaginal probe for use when the patient has her uterus.
Figure 6A:
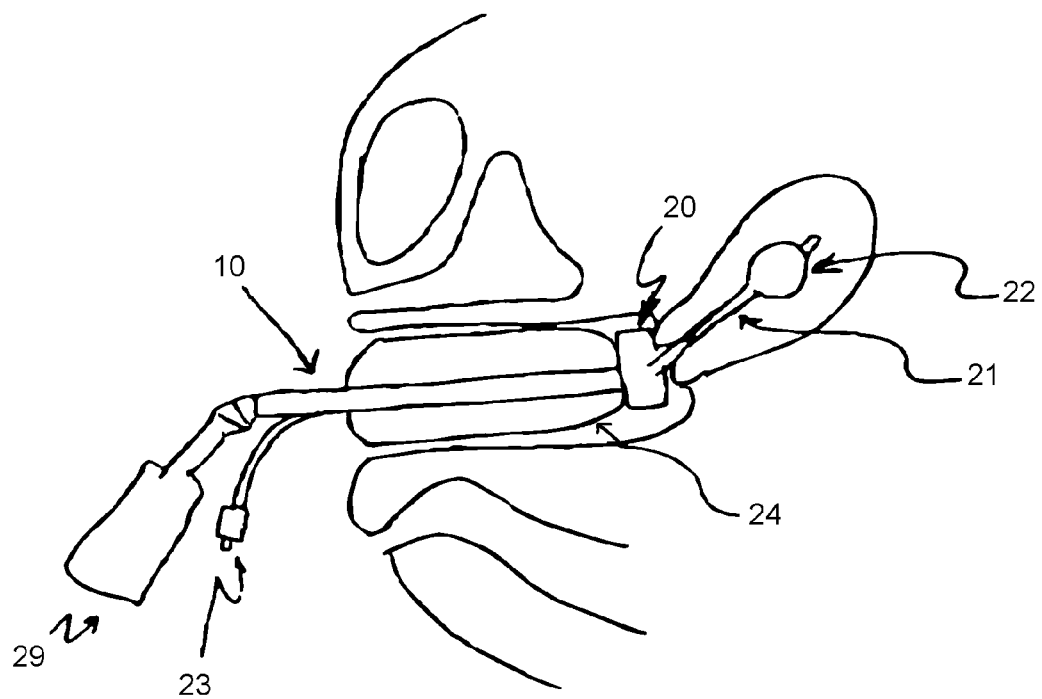

FIG. 6 illustrates a configuration of the uterine manipulator, which includes a handle (29), a shaft (10), a disc (20) which is positioned on the cervix, and an intracervical probe (21) with a balloon that may be inflated (22) through an inflation port near the handle (23). The device may have an attachment (24) with a conductive surface that delineates the posterior or anterior vagina which may slide up along the shaft (10). FIG. 6A shows an alternative embodiment in which the attachment (24) delineates both the anterior and posterior vagina.

Figure 7:
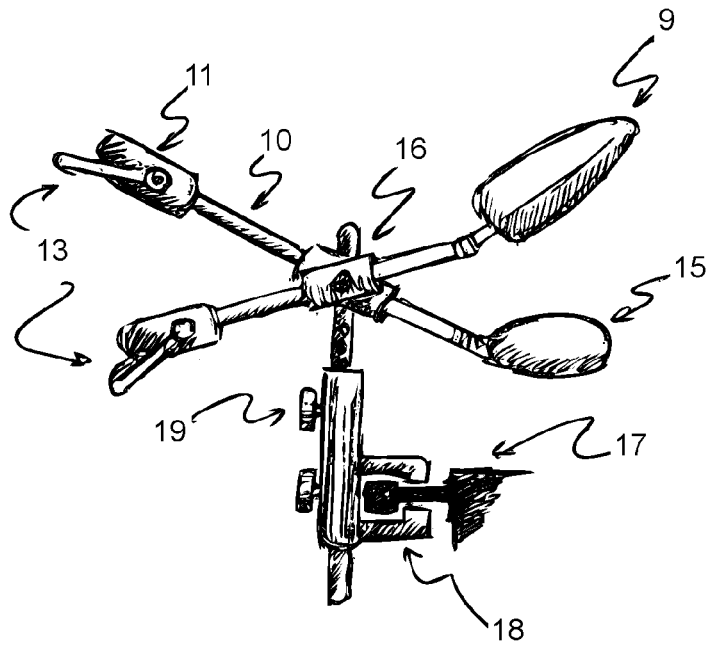
FIG. 7 demonstrates the vaginal and rectal probes attached to one another and attached to a fixed structure, such as the operating room table.

FIG. 7 demonstrates vaginal and rectal probes connected with a connector device (16) and which may be attached to the operating room table (17) with an attachment clamp (18). An adjustment clamp (19) may be used to raise or lower the manipulators and the individual devices may be advanced or withdrawn through the connector device (16).

Figure 8:
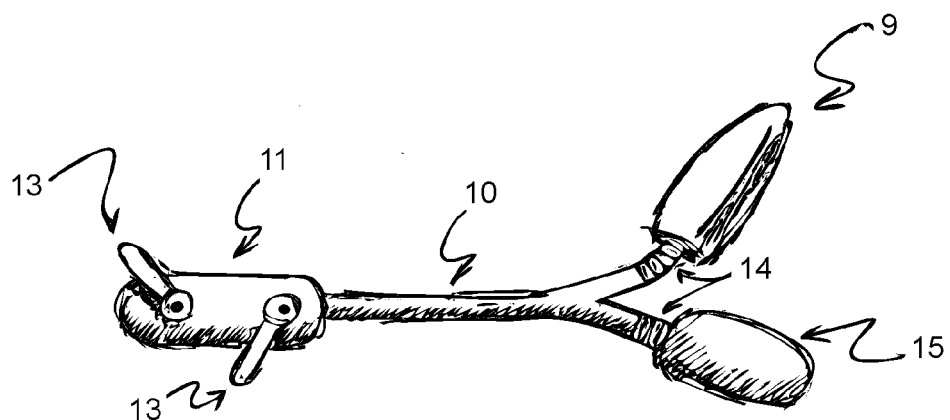
FIG. 8 demonstrates a single-shaft instrument that has both a vaginal and rectal probe, each of which may be deflected independently.

FIG. 8 demonstrates a single-shaft instrument that has both a vaginal (9) and a rectal (15) probe. There are two separate deflection devices (13) on the single handle (11), which may be used to independently tilt either the vagina or the rectum anteriorly or posteriorly.

Figure 9A:
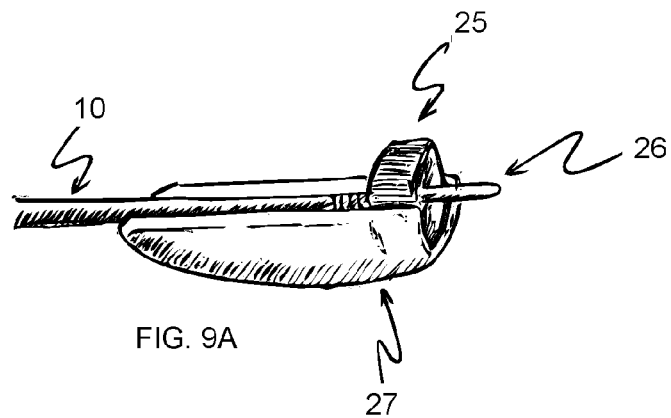
FIGS. 9A-B illustrate another embodiment of the vaginal portion of the device, when the patient has a uterus. The cervix may be flexed anteriorly or posteriorly while the posterior vagina is delineated with a conductive surface.

FIG. 9A illustrates another embodiment of the vaginal portion of the device, when the patient has a uterus. The device has a shaft (10), an articulating cup (25) that fits over the cervix, and a probe (26) that is placed into the endocervical canal and may have an inflatable intrauterine balloon. The device may have an intravaginal delineating portion (27) that may be circumferential or may delineate only part of the vaginal circumference that may have a conducting surface in order to detect penetration of the vaginal wall with a needle, tack, staple or other conducting device, such as a needle with suture placed laparoscopically.

Figure 9B:
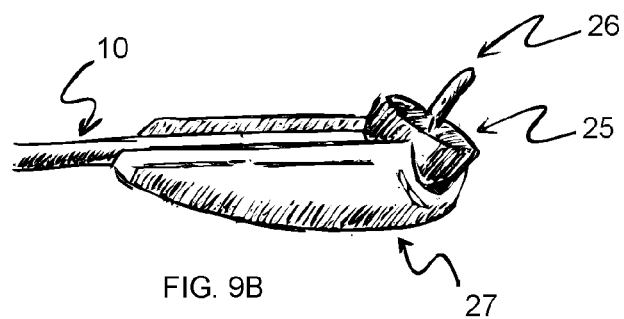

FIG. 9B illustrates the same device as in FIG. 9A, with the articulating cervical cup anteverted (25). The device may have several interchangeable cups of various sizes to fit over different cervical sizes.

The invention claimed is:

1. An electrical tissue injury detection system comprising:
a device comprising:
   a first probe comprising:
      a handle;
      a shaft extending from the handle; and
      a first delineator at a distal end of the shaft, the delineator sized and shaped to conform to an interior of a first hollow organ, the delineator having an electrically conductive outer surface;
   a second probe comprising:
      a handle;
      a shaft extending from the handle; and
      a second delineator at a distal end of the shaft, the delineator sized and shaped to conform to an interior of a second hollow organ, the delineator having an electrically conductive outer surface;
   wherein the first probe is held in proximity to the second probe by a connector that allows the first and second probes to pivot, advance, and retract relative to one another;
an electrical connection extending from an electrically conductive outer surface of a probe of the device;
an electrically conductive surgical tool from which extends an electrical connection;
a meter, connected to the device and the tool through the electrical connections, that measures an electrical parameter between the device and the tool and produces a warning signal when the electrical parameter changes in a manner that indicates perforation of an anatomic structure by the surgical tool; and
a power source electrically connected to at least one of the device, the tool, and the meter.

2. The device of claim 1, further comprising a deflector operative to flex at least one of the first probe and the second probe at a joint proximate the delineator.

3. The device of claim 1, further comprising a clamp assembly attached to the connector, the clamp assembly comprising an adjustment clamp and an attachment clamp.

4. The device of claim 1, wherein the first probe is a vaginal probe, and the first delineator is sized and shaped to conform to a vaginal interior.

5. The device of claim 4, wherein the first delineator has an oval, biconvex, or truncated biconvex cross section.

6. The device of claim 4, wherein the vaginal probe further comprises an articulating cup distal to the first delineator and an intracervical probe extending distally from the cup.

7. The device of claim 6, further comprising an inflatable balloon extending from the intracervical probe and an inflation port communicating with the balloon.

8. The device of claim 1, wherein at least one of the first probe and the second probe further comprises a light source.

* * * * *